(12) United States Patent
Ferree (10) Patent No.: US 8,162,993 B2
(45) Date of Patent: Apr. 24, 2012

(54) METHODS OF ANTERIOR FIXATION AND STABILIZATION OF A SPINAL SEGMENT

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 1147 days.

(21) Appl. No.: 11/945,994

(22) Filed: Nov. 27, 2007

(65) Prior Publication Data

US 2008/0125779 A1 May 29, 2008

Related U.S. Application Data

(60) Provisional application No. 60/861,499, filed on Nov. 28, 2006.

(51) Int. Cl.
*A61B 17/88* (2006.01)

(52) U.S. Cl. ..... 606/279; 606/263; 606/228; 623/17.11; 623/13.14

(58) Field of Classification Search ............ 606/60, 606/246, 263, 279, 280, 70–71, 281, 283–286, 606/300–301, 228, 232, 74, 103, 151–156; 623/17.11–17.16, 13.13–13.14
See application file for complete search history.

(56) References Cited

U.S. PATENT DOCUMENTS

| | | | | |
|---|---|---|---|---|
| 6,093,205 | A * | 7/2000 | McLeod et al. | 623/17.16 |
| 6,645,211 | B2 * | 11/2003 | Magana | 606/247 |
| 7,090,675 | B2 * | 8/2006 | Songer | 606/247 |
| 7,776,069 | B2 * | 8/2010 | Taylor | 606/249 |
| 2001/0027319 | A1 * | 10/2001 | Ferree | 606/61 |
| 2002/0120269 | A1 * | 8/2002 | Lange | 606/61 |
| 2004/0260287 | A1 * | 12/2004 | Ferree | 606/61 |
| 2006/0084985 | A1 * | 4/2006 | Kim | 606/61 |
| 2006/0089646 | A1 * | 4/2006 | Bonutti | 606/61 |
| 2007/0005062 | A1 * | 1/2007 | Lange et al. | 606/61 |
| 2007/0073293 | A1 * | 3/2007 | Martz et al. | 606/61 |
| 2007/0168035 | A1 * | 7/2007 | Koske | 623/17.13 |
| 2007/0239158 | A1 * | 10/2007 | Trieu et al. | 606/61 |
| 2008/0262550 | A1 * | 10/2008 | Ferree | 606/263 |
| 2010/0076492 | A1 * | 3/2010 | Warner et al. | 606/279 |
| 2010/0152779 | A1 * | 6/2010 | Allard et al. | 606/279 |
| 2010/0211108 | A1 * | 8/2010 | Lemole, Jr. | 606/264 |

* cited by examiner

*Primary Examiner* — Eduardo C Robert
*Assistant Examiner* — Michelle C Eckman
(74) *Attorney, Agent, or Firm* — Pandiscio & Pandiscio (57) ABSTRACT

Methods for spinal stabilization operative to prevent lateral bending, extension, and rotation across two or more adjacent vertebrae are described. Broadly, the method includes placing two or more anchors at each vertebral level, passing one or more sutures through each anchor at each level, applying tension to the sutures and joining the sutures in a cross-braced arrangement over the disc space between two or more vertebrae to prevent lateral bending, extension, and rotation of the spinal segment. The sutures can be welded in any combination of diagonal and vertical patterns across the adjacent vertebrae. In some embodiments, two or more sutures can be threaded through some of the suture anchors such that multiple vertebral levels can be joined in a cross-braced arrangement. Two or more sutures can also be used in multiple anchors in two adjacent vertebrae to provide additional reinforcement or stabilization across different portions of the two vertebrae. The sutures reinforcing different portions of the vertebrae can have different breakage strength and different elastic properties. The invention may be used on the cervical, thoracic, lumbar, or sacral regions of the spine.

22 Claims, 7 Drawing Sheets

METHODS OF ANTERIOR FIXATION AND STABILIZATION OF A SPINAL SEGMENT

RELATED APPLICATIONS

This application claims the benefit of provisional application 60/861,499, filed Nov. 28, 2006, entitled "Annulus and Spinal Ligament Reconstruction." This application is related to co-pending application 60/808,795, filed May 26, 2006, entitled "Fastening Assemblies for Disc Herniation Repair and Methods of Use." The application is also related to U.S. Pat. Nos. 6,248,106 and 6,423,065. All of the above-referenced patent and applications are hereby expressly incorporated by reference in their entirety.

FIELD OF THE INVENTION

The subject invention resides in methods and apparatus for reconstructing the annulus fibrosis (AF) of a spinal disc and the ligaments of the spine. The invention is particularly well suited to the prevention of extrusion of material or devices placed into the disc space and to the prevention of excessive spinal motion.

BACKGROUND

The human intervertebral disc is an oval to kidney bean-shaped structure of variable size depending on the location in the spine. The outer portion of the disc is known as the annulus fibrosis (AF). The annulus fibrosis is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The annulus fibrosis contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the annulus fibrosis. As discussed in co-pending U.S. patent application Ser. No. 10/407,554 and U.S. Pat. No. 6,878,167, the content of each being expressly incorporated herein by reference in their entirety, the posterior portion of the annulus fibrosis has abundant pain fibers.

Herniated nucleus pulposus (HNP) occurs from tears in the annulus fibrosis. The herniated nucleus pulposus often allies pressure on the nerves or spinal cord. Compressed nerves cause back and leg or arm pain. Although a patients symptoms result primarily from pressure by the nucleus pulposus, the primary pathology lies in the annulus fibrosis.

Surgery for herniated nucleus pulposus, known as microlumbar discectomy (MLD), only addresses the nucleus pulposus. The opening in the annulus fibrosis is enlarged during surgery, further weakening the annulus fibrosis. Surgeons also remove generous amounts of the nucleus pulposus to reduce the risk of extruding additional pieces of nucleus pulposus through the defect in the annulus fibrosis. Although microlumbar discectomy decreases or eliminates a patient's leg or arm pain, the procedure damages weakened discs.

SUMMARY

A portion of the annulus fibrosis and a portion of the ligaments of the spine are excised to allow insertion of materials and devices into the disc space. For example, a portion of the anterior half of the annulus fibrosis and a portion of the anterior longitudinal ligament (ALL) are excised to enable insertion of bone growth promoting materials and fusion devices in interbody fusion procedures. Removal of portions of the annulus fibrosis and anterior longitudinal ligament increase the flexibility of the spine and allow excessive motion of the spine. For example, removal of the tissues mentioned permits excessive spinal extension, lateral bending, and axial rotation. Destabilizing the spine decreases the chance of a successful fusion. The invention may be used to increase the stiffness of the operated segment of the spine. Increasing the stiffness of the spine facilitates spinal fusion.

A portion of the annulus fibrosis and a portion of the anterior longitudinal ligament are also excised to enable insertion of motion preserving devices into the disc. For example, Total Disc Replacements (TDRs) and Nucleus Replacements (NRs) are often inserted through the anterior portion of discs. Excessive spinal extension, lateral bending, and axial rotation following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The present invention provides methods for spinal stabilization operative to prevent lateral bending, extension, and rotation across adjacent vertebrae. Broadly, the method includes placing two or more anchors at each vertebral level, passing one or more sutures through each anchor at each level, applying tension to the sutures and joining the sutures in a cross-braced arrangement over the disc space to prevent lateral bending, extension, and rotation of the spinal segment.

In some embodiments, six anchors can be used to join multiple levels of vertebrae. Two anchors are placed in each vertebra. The anchors placed in the cranial and caudal vertebrae each have at least one elongate member, such as a suture, extending therethrough. The anchors in the medial vertebra have at least two elongate members extending therethrough. Tension is applied to the elongate members and the elongate members extending from the medial anchor are attached in a crossing pattern with the elongate members extending from the cranial and caudal anchors having left and right generally vertically extending segments and diagonal connections between upper and lower end regions of each vertically extending segment.

In some embodiments, the sutures are joined by welding. In some embodiments, a mesh patch can be placed between the sutures and the vertebrae to provide a cushion between the sutures and the bone and reduce friction on the sutures and the suture welds. In some embodiments, the material for the mesh can be selected such that connective tissue will grow into and over the mesh in vivo, forming a synthetic tendon-like layer that further cushions and protects the sutures. In some embodiments, an anti-adhesion patch can be placed over the exposed portions if the sutures and the suture anchors.

In an alternative embodiment, multiple anchors and sutures can be used to provide additional stabilization/fixation across two adjacent vertebrae. In some embodiments, six or more anchors can be placed in two adjacent vertebrae, each anchor having at least one suture extending therethrough. The sutures can be arranged in any combination of vertical and diagonal patterns across the two adjacent vertebrae and joined together to prevent lateral bending, extension, and rotation of the spinal segment. Tension can be applied to the sutures prior to joining them together to vary the resistance to spinal extension, lateral bending and axial rotation extension as necessary. In some embodiments, the sutures can be made of different material and have different properties.

DETAILED DESCRIPTION

Figure 1A:
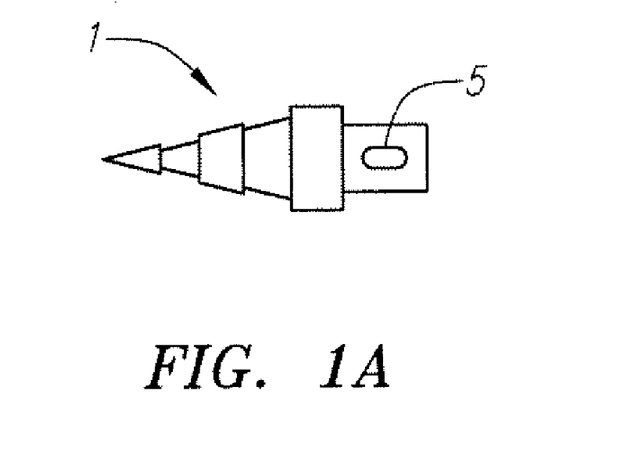
FIG. 1A is a lateral view of a suture anchor with a single eyelet.
Figure 1B:
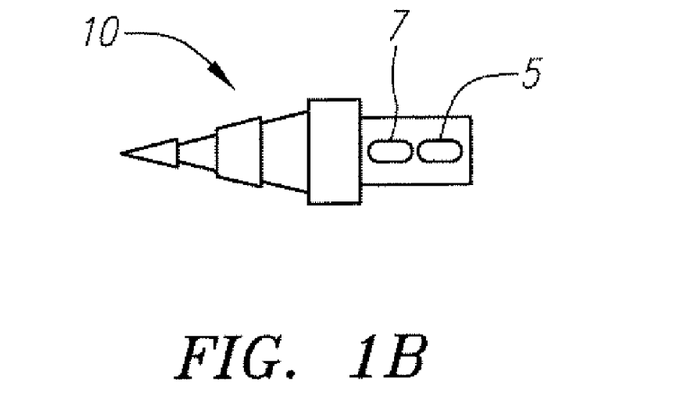
FIG. 1B is a lateral view of a suture anchor with two eyelets

FIG. 1A is a lateral view of a suture anchor 1 with one eyelet 5. FIG. 1B is a lateral view of a suture anchor 10 with two eyelets 5 and 7. The suture anchors comprise anchor 1 and 10 having a first portion capable of being inserted into or otherwise attached to a bone, such as vertebrae. Anchor 1 has a second portion with opening 5 adapted to receive a suture therethrough. Anchor 1 also has a second portion with openings 5 and 7 each adapted to receive a suture therethrough. In one embodiment, anchor 10 is a screw having two holes through the head of the screw.

The anchors 10 can vary in size from about 3 to about 12 mm in diameter and about 4 to about 40 mm in length. For example, anchors having a diameter of about 3 mm and a length of about 7 mm can be used in the anterior portions of cervical vertebrae. Additionally, anchors having a diameter of about 8 mm and a length of about 35 mm can be used in the anterior portions of lumber vertebrae. The anchors are preferably made of an MRI-compatible material. For example, the anchors can be made of titanium, plastic, or other material. The anchors can additionally be coated with a material, such as hydroxyappetite, that promotes the in-growth of bone. In an alternative embodiment, the anchors can be hollow and filled with a material that promotes bone in-growth.

Figure 2A:
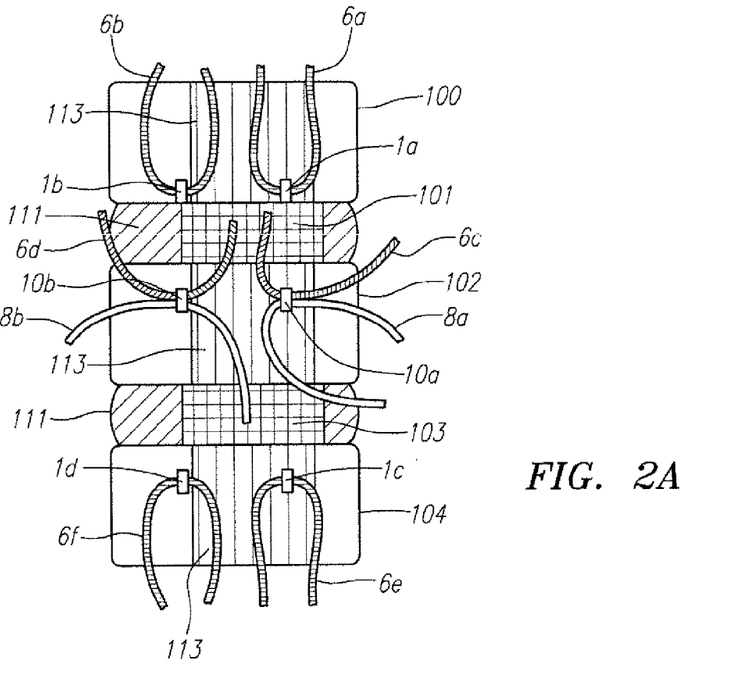
FIG. 2A is an anterior view of an embodiment for joining three adjacent vertebrae.

In one embodiment, anchors 1 and 10 can be used to join multiple levels of vertebrae. FIG. 2A is an anterior view of the spine with intradiscal devices inserted in the disc spaces between three adjacent vertebrae 100, 102 and 104. Six suture anchors 1a-d and 10a-b are used to join the three adjacent vertebrae 100, 102 and 104. The anterior portion of the annulus fibrosis 111 and the anterior longitudinal ligament 113 were excised to permit insertion of intradiscal devices 101 and 103, such as a nucleus replacement (NR), bone graft, spinal cage, or TDR, into the disc space between vertebrae 100 and 102 and the disc space between vertebrae 102 and 104. Two suture anchors 1a, 1b were placed into the vertebra 100 cranial to the intradiscal device 101, two suture anchors 10a, 10b were placed into vertebra 102 and two suture anchors 1c, 10d were placed into the vertebra 104 caudal to the intradiscal device 103. The anchors 1a-d placed in the cranial and caudal vertebrae 100, 104 have a single eyelet for threading a single suture 6a,b,e,f each. The anchors 10a,b placed in the medial vertebrae 102 have two eyelets, as shown in FIG. 1B, for threading two sutures 6c,d and 8a,b each. In some embodiments, the cranial and caudal anchors can also have two eyelets for threading a second suture.

Sutures 6a,b,e,f are threaded through the single eyelets in anchors 1 a,b,c,d respectively such that first and second ends of each suture 6a,b,e,f extend from anchors 1 a,b,c,d. Sutures 6c,d are threaded through first eyelets in anchors 10a,b and sutures 8a,b are threaded through second eyelets in anchors 10a,b such that first and second ends of sutures 6c and 8a extend from anchor 10a and first and second ends of sutures 6d and 8b extend from anchor 10b.

In some embodiments, the sutures can be monofilament or multifilament configurations of nylon, polypropylene, polyester, polyethylene, or other material. For example in one embodiment, the sutures can be made from a #5 polyester multifilament material. In another embodiment, the sutures can be made of a #5 resorbable multifilament suture such as VICRYL™ (Ethicon, NJ). In other embodiments, suture materials can be selected for specific characteristics. For example, rigid, semi-rigid or elastic materials may be selected. In embodiments of the invention used in spinal fusion procedures relatively inelastic sutures are preferably used. In other embodiments, the sutures can be made of materials than can be welded together.

In some embodiments, the sutures 6a-f and 8a,b can be different sizes and/or made of different materials such that the sutures have different tensile strength or other properties. For example, in one embodiment, one set of sutures 6a-f could be a #5 polyester multifilament material. The other set of sutures 8a,b could be made of VICRYL™. Alternatively, in some embodiments, one set of sutures could be more elastic than the second set of sutures. For example, one set of sutures 6a-f could reversibly stretch about 1 to about 10 mm. The other set of sutures 8a,b could reversibly stretch about 5 to about 8 mm.

Figure 2B:
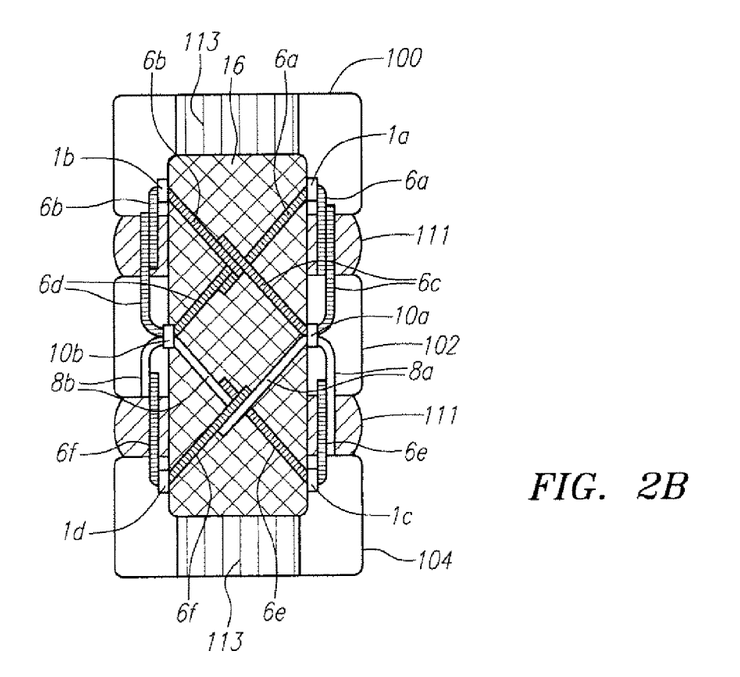
FIG. 2B is an anterior view of the embodiment in FIG. 2A with the sutures welded together in a cross-braced pattern.

As shown in FIG. 2B, the medial ends of sutures 6a-f and 8-a,b are joined in an axial and criss-crossed pattern over the disc space between vertebrae 100, 102 and 104. In the illustrated embodiment, the medial ends of the sutures 6a-b and 6c-d from the anchors 1a,b and 10a,b were welded together over the disc space between vertebrae 100 and 102 and the lateral ends of the sutures 6a-b and 6c-d were welded together to create vertical fixation suture arms. Similarly, the medial ends of sutures 8a-b and 6e-f were welded together over the disc space between vertebrae 102 and 104 while the lateral ends of the sutures 8a-b and 6e-f were welded together to create vertical fixation suture arms. This configuration joins the three adjacent vertebrae 100, 102 and 104 and forms "Xs" over the disc space between vertebrae 100 and 102, and between vertebrae 102 and 104. The pattern of the sutures over the disc space advantageously provides an arrangement that resists and/or limits extension, lateral bending and torosional/rotational stresses. The vertical fixation suture arms resist extension of the spine. The diagonal fixation suture arms resist lateral bending, axial rotation as well as extension of the spine.

The ends of sutures 6a-f and 8a,b can be joined together by any suitable method known in the art such as a knot, crimping, melting, welding or otherwise fusing the two ends of the suture. In one embodiment, shown in FIG. 21B, the ends of sutures 6a-f and 8a,b can be welded together. The weld is preferably caused by heat-generating or heat-conducting instruments. The heat may be generated ultrasonically or by other means. Instruments with special tips may be used to weld the sutures within deep areas of the body. For example, instruments that are about 15 to abut 45 cm in length may be needed to weld sutures in the abdomen. The welding instruments are preferably about 4 to about 8 mm in diameter. In some embodiments, tension can be applied to the sutures 6a-f, 8a,b before the sutures 6a-f, 8a,b are welded together.

In addition, in some embodiments, as shown in FIG. 2B, a piece of porous mesh material 16 can be placed between the fixation sutures 6a-f, 8a,b and the spine before welding the sutures 6a-f, 8a,b together. The mesh 16 acts as scaffolding for connective tissue in-growth from the annulus fibrosis 111, the anterior longitudinal ligament 113, and the vertebrae 100, 102, and 104. The pores within the mesh 16 are preferably about 0.1 to 2.0 mm in diameter. Mesh piece 16 may be made of synthetic materials such as polyester, polypropylene, ePTFE, or polyethylene. Alternatively, the mesh could be made of natural material such as autograft, allograft, or xenograft tissues such as acellular dermis, swine intestinal submucosa, ligaments, facia, or tendon. The mesh 16 should extend over both sides of the anterior longitudinal ligament 113 and the annulus fibrosis 111 on either side of the annular window. The connective tissue, the mesh 16, and the fixation sutures 6a-E, 8a,b at least partially reproduce the function of the annulus fibrosis and the anterior longitudinal ligament. The components also prevent extrusion of tissue that resides within the disc, such as the nucleus pulposus, or materials or devices that are placed within the disc, such as intradiscal devices 101 and 103. Radio-opaque markers could be added to the mesh 16 and or the fixation sutures 6a-f, 8a,b to help identify the location of the components on x-ray. For example, metal wires or staples could be included in mesh or fixation sutures. Alternatively, radio-opaque materials such as barium or other contrast agents may be used to "dye" the mesh or fixation sutures.

In some embodiments, the sutures and anchors may be covered with an anti-adhesion component as described in co-pending patent application 60/808,795, filed May 26, 2006, entitled "Fastening Assemblies for Disc Herniation Repair and Methods of Use," hereby expressly incorporated by reference in its entirety. For example, an anti-adhesion cover 20 could be attached to the fixation sutures 6a-f, 8a,b and/or the porous mesh 16. In some embodiments, the anti-adhesion cover can be a piece of ePTFE. Alternatively, the anti-adhesion cover could also be made of autograft, allograft, or xenograft tissues such as acellular dermis, swine intestinal submucosa, ligaments, facia, or tendon.

Figure 2C:
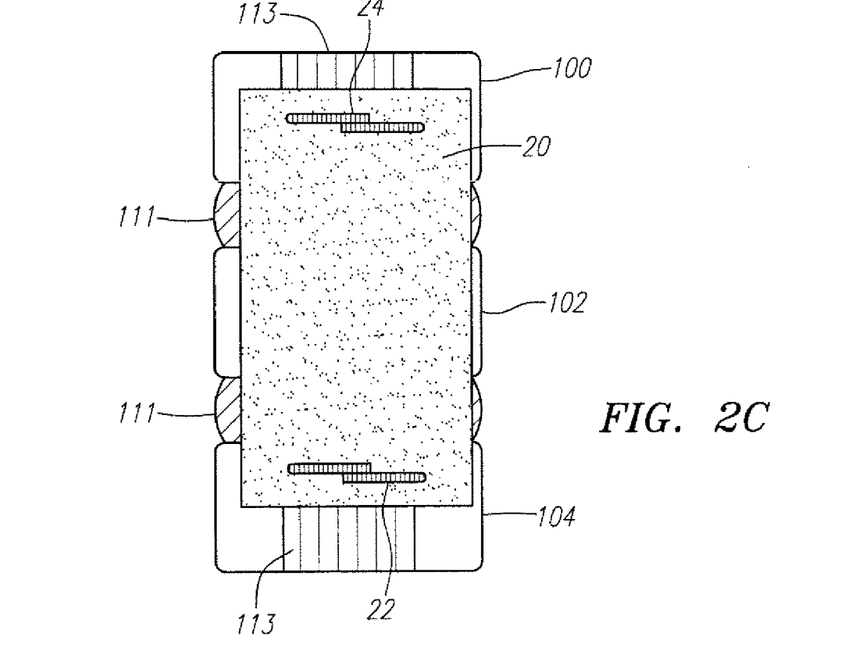
FIG. 2C illustrates an anterior view of the embodiment in FIG. 2B with an anti-adhesion cover placed over the fixation sutures and suture anchors.
Figure 2D:
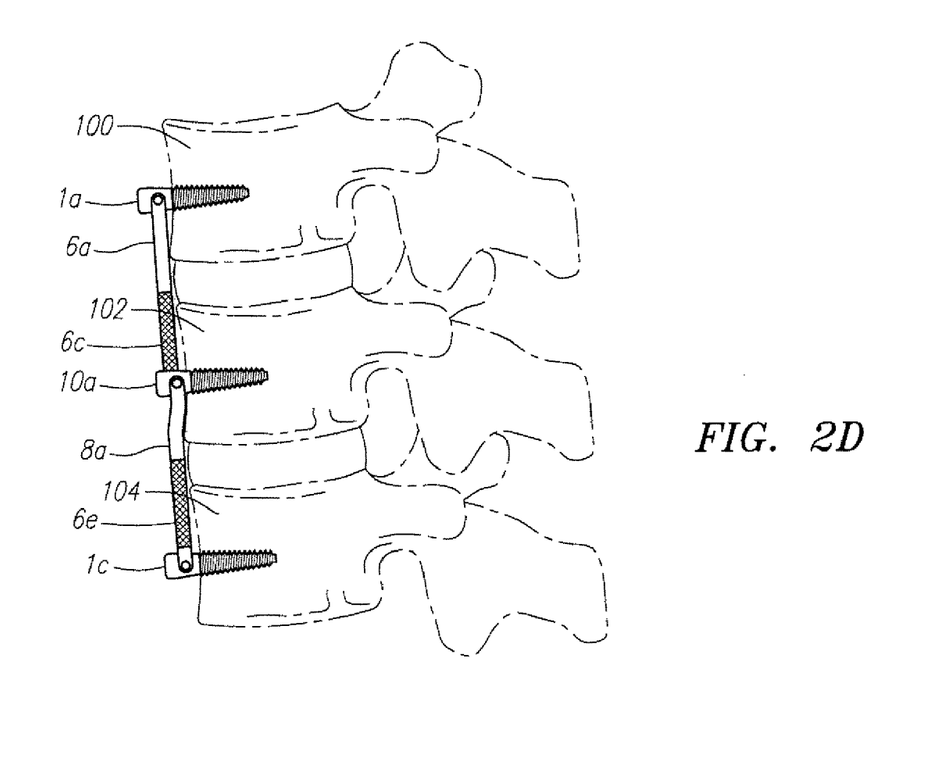
FIG. 2D illustrates a lateral view of the embodiment in FIG. 2A.

In some embodiments, as shown in FIG. 2C, two connecting sutures 22 and 24 can be used to connect the anti-adhesion patch 20 to mesh patch 16. The connecting sutures 22 and 24 are passed through mesh patch 16 and anti-adhesion cover 20 and then joined together, for example by welding or any other suitable method, over the anti-adhesion cover 20 to hold the anti-adhesion cover against the vertebrae 100, 102 and 104 and annulus fibrosis 111. Anti-adhesion component 20 is sized to extend over the anchors 1a-d, 10a,b, mesh 16, fixation sutures 6a-f and 8a,b, the cut edges of the annulus fibrosis 111 and the cut edges of the anterior longitudinal ligament 113. The mesh 16 and anti-adhesion 20 components may also be connected with alternative fastening methods known in the art. In an alternative embodiment a single connecting suture can be passed through the mesh patch 16 and anti-adhesion cover 20 and then welded, or otherwise joined, together to hold the anti-adhesion cover 20 against the vertebrae 100, 102 and 104 and annulus fibrosis 111. Covering the stiff ends of the sutures with the anti-adhesion patch 20 protects the suture welds from peeling forces due to friction from adjacent structures and helps prevent injury to delicate structures such as nerves, blood vessels, and the esophagus that lie directly over the stiff ends of the sutures and exposed portions of the suture anchors.

Figure 3A:
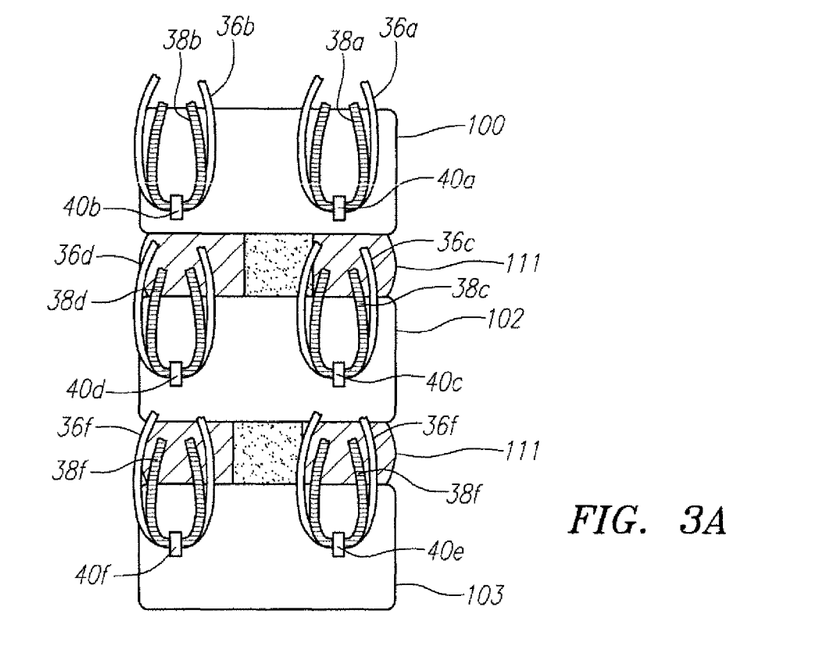
FIG. 3A is an anterior view of an alternative embodiment for joining multiple vertebrae of the spine using two sutures in each suture anchor.

In an alternative embodiment, as shown in FIG. 3A, the suture anchors 40a,b,e,f in the cranial and caudal vertebrae 100, 104 can have two eyelets for threading a second suture as well as the anchors 40c,d in the medial vertebra 102. Here, sutures 36a,b,c,d,e,f are threaded through the first eyelets in anchors 40a,b,c,d,e,f respectively such that first and second ends of each suture 36a,b,c,d,e,f extend from anchors 40a,b,c,d,e,f. Sutures 38a,b,c,d,e,f are threaded through second eyelets in anchors 40a,b,c,d,e,f such that first and second ends of sutures 38a,b,c,d,e,f also extend from anchors 40a,b,c,d,e,f.

Figure 3B:
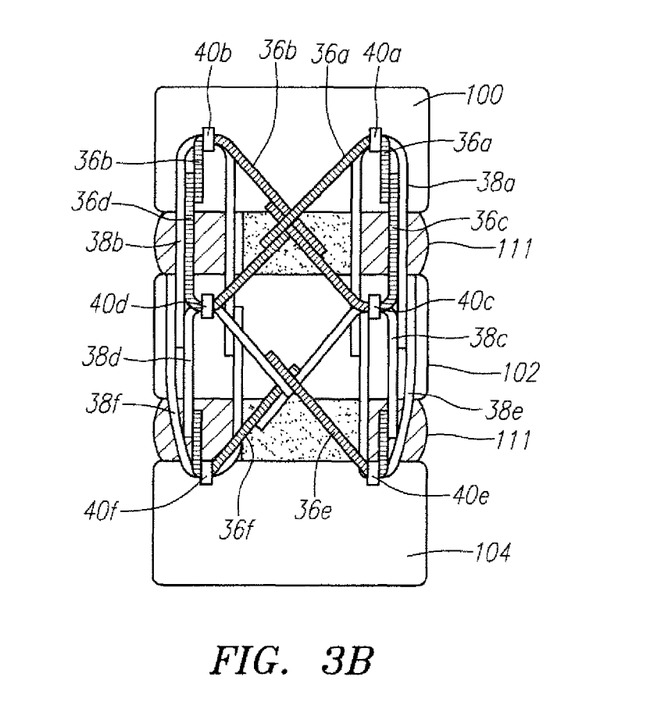
FIG. 3B is an anterior view of the embodiment in FIG. 3A with the first sutures welded together in a cross-braced pattern and the second sutures welded together in a vertical pattern.

As shown in FIG. 3B, the medial ends of sutures 36a,b,c,d,e,f and 38-c,d are joined in an axial and criss-crossed pattern over the disc space between vertebrae 100, 102 and 104. In the illustrated embodiment, the medial ends of the sutures 36a-b and 36c-d from the anchors 40a,b,c,d were welded together over the disc space between vertebrae 100 and 102 to create diagonal fixation suture arms and the lateral ends of the sutures 36a,b and 36c,d were welded together to create vertical fixation suture arms. Similarly, the medial ends of sutures 38c,d and 36e,f were welded together over the disc space between vertebrae 102 and 104 diagonal fixation suture arms while the lateral ends of the sutures 38c,d and 36e,f were welded together to create vertical fixation suture arms. In addition, medial and lateral ends of the second sutures 38a and 38e and 38b and 38f in the second eyelets in suture anchors 40a,b,e,f were welded together to create vertical fixation suture arms joining the cranial and caudal vertebrae 100 and 102. Tension can be applied to each of the sutures prior to welding. The sutures 38a,b,e,f are preferably longer than sutures 36a,b,c,d,e,f and 38c,d so that they can extend between vertebrae 100 and 104. In some embodiments, the sutures 38a,b,e,f can also be made of a different material having different breakage strength. This configuration joins the three adjacent vertebrae 100, 102 and 104 in arrangement including "Xs" over the disc space between vertebrae 100 and 102, and between vertebrae 102 and 104 as well as vertical suture arms extending between vertebrae 100 and 104. The pattern of the sutures over the disc space advantageously provides an arrangement that resists and/or limits extension, lateral bending and torosional/rotational stresses. The vertical fixation suture arms resist extension of the spine. The diagonal fixation suture arms resist lateral bending, axial rotation as well as extension of the spine.

In addition, as discussed above with respect to the embodiment in FIGS. 2A-D, a piece of porous mesh material can be placed between the fixation sutures 36a-f and 38a-f and the spine before welding the sutures 36a-f and 38a-f together. Likewise, an anti-adhesion cover can be placed over the exposed portions of the sutures 36a-f and 38a-f and suture anchors 40a-f anchors to protect the suture welds from peeling forces due to friction from adjacent structures and helps prevent injury to delicate structures such as nerves, blood vessels, and the esophagus that lie directly over the stiff ends of the sutures and exposed portions of the suture anchors.

Figure 4A:
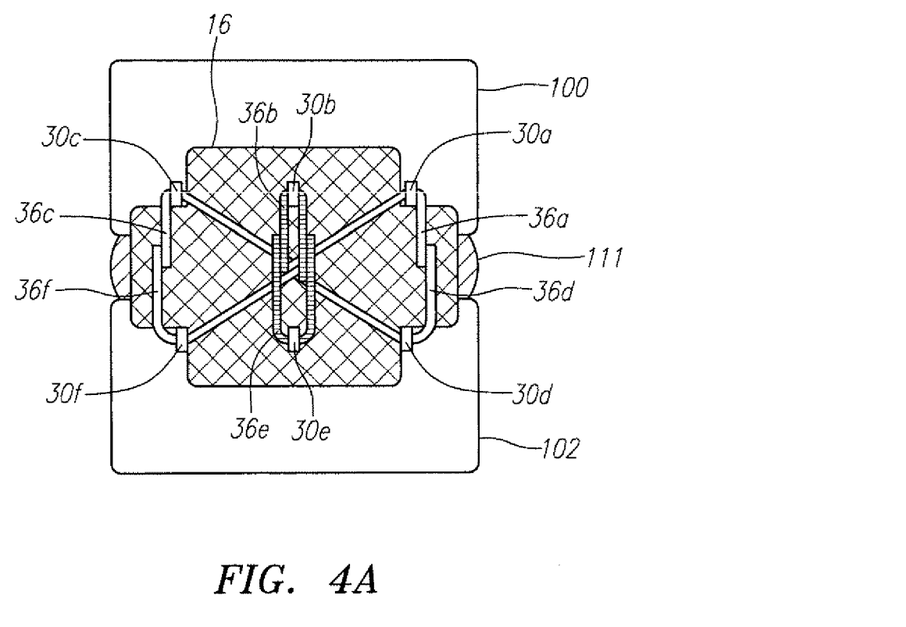
FIG. 4A is an anterior view of an alternative embodiment for joining two adjacent vertebrae using three anchors in each vertebrae.

In an alternative embodiment, multiple anchors and sutures can be used to provide additional stabilization/fixation across two adjacent vertebrae. As shown in FIG. 4A, six anchors 30a-f can be used to join two adjacent vertebrae 100 and 102. In alternative embodiments, more than six or less than four anchors can be used. Here, anchors 30a,b,c were placed in the cranial vertebra 100. Anchors 30d,e,f were placed in the caudal vertebra 102. Sutures 36a,b,c,d,e,f were threaded through anchors 30a,b,c,d,e,f respectively. First and second ends of sutures 36b,e from central anchors 30b,e were welded together to create a pair of vertical fixation members 36be across the central portion of vertebrae 100,102. Medial ends of sutures 36a and f and of 36c and d were welded together to create diagonal fixation members 36af and 36cd extending across vertebrae 100 and 102. Lateral ends of sutures 36a and d and of 36c and f were welded together to create vertical fixation members 36ad and 36cf extending across the lateral portions of vertebrae 100, 102. Tension is applied to the ends of sutures 36a-f before welding together. A piece of porous mesh material 16 can be placed between the fixation sutures 36a-f and the spine before welding the sutures 36a-f together. As discussed above in detail with respect to the embodiments in FIGS. 2A-D, an anti-adhesion cover, such as ePTFE can be placed over the exposed portions of the suture anchors 30a-f and sutures 36a-f to protect the suture welds from peeling forces due to friction from adjacent structures and help prevent injury to delicate structures such as nerves, blood vessels, and the esophagus that lie directly over the stiff ends of the sutures and exposed portions of the suture anchors.

Here, the vertical fixation members 36be from the central pair of anchors 30b,e resist extension of the spine. The vertical fixation members 36ad and 36cf from the lateral pairs of anchors 30a,c,d,f resist lateral bending and the diagonal fixation members 36cd and 36af resist axial rotation as well as lateral bending and extension of the spine. The flexible fixation members that extend from the anchors may have different breakage strength and different elastic properties. For example, the flexible fixation members 36b,e from the central pair of anchors 30b,e may have a higher breakage strength than the flexible fixation members 36a,c,d,f from the lateral pairs of anchors 30a,c,d,f, thereby restricting extension of the spine more than lateral bending or axial rotation. In addition, the tension applied to each suture prior to welding can be varied depending on the breakage strength of the suture material and the desired resistance to motion in a certain direction. For example, more tension can be applied to the sutures comprising the vertical fixation members to create more resistance to spinal extension. Alternatively, more tension can be applied to the sutures comprising the diagonal fixation members to create more resistance to axial rotation or the sutures comprising the vertical fixation members on the lateral sides of the vertebrae to create more resistance to lateral bending as well as extension.

Figure 4B:
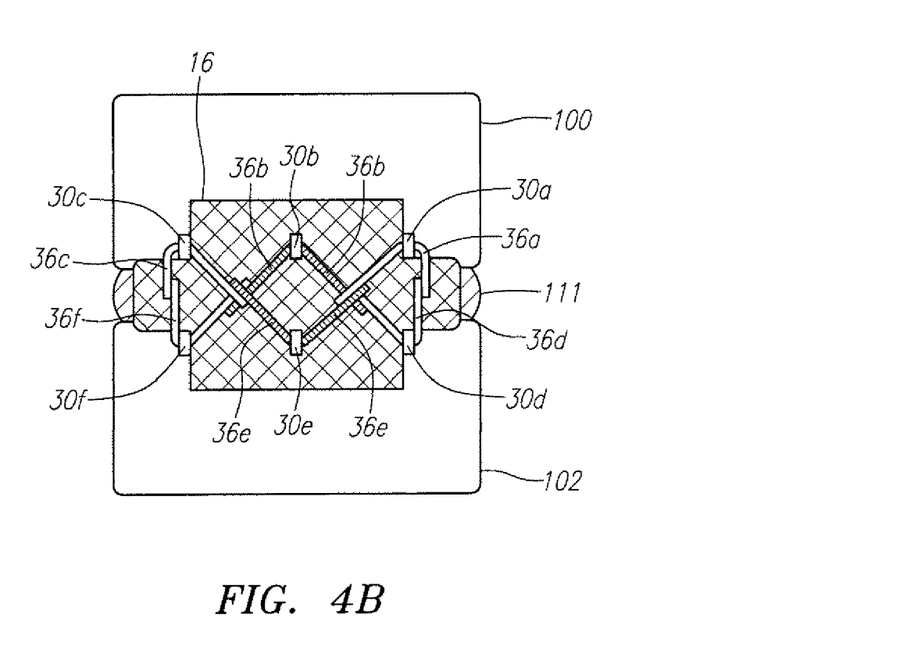
FIG. 4B is an anterior view of an alternative embodiment for joining two adjacent vertebrae using three anchors in each vertebrae.

In an alternative embodiment, the sutures 36a,b,c,d,e,f extending from suture anchors 30a-f can be welded together in any combination diagonal, horizontal and or vertical patterns across the adjacent vertebrae to alter the resistance to spinal extension, lateral bending and axial rotation extension as necessary. For example, as shown in FIG. 4B, in one embodiment, lateral ends of sutures 36c and 36f and sutures 36a and 36d are welded together to create vertical fixation arms 36cf and 36ad. Medial ends of sutures 36a,c,d,f are welded to first and second ends of sutures 36*b,e* to create diagonal fixation arms 36*ae,bd,bf,ce*. Such an embodiment emphasizes resistance axial rotation by providing an additional set of diagonal fixation arms across the two vertebrae. The diagonal fixation arms also lie over the opening in the annulus fibrosis and help prevent extrusion of material through the opening.

Figure 5A:
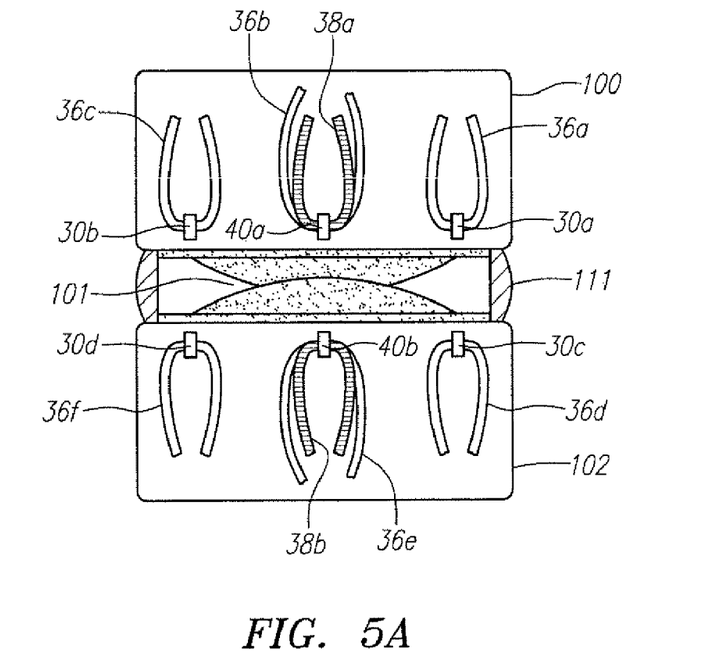
FIG. 5A is an anterior view of an alternative embodiment for joining two adjacent vertebrae using three anchors in each vertebrae and a second set of sutures in the central anchors.
Figure 5B:
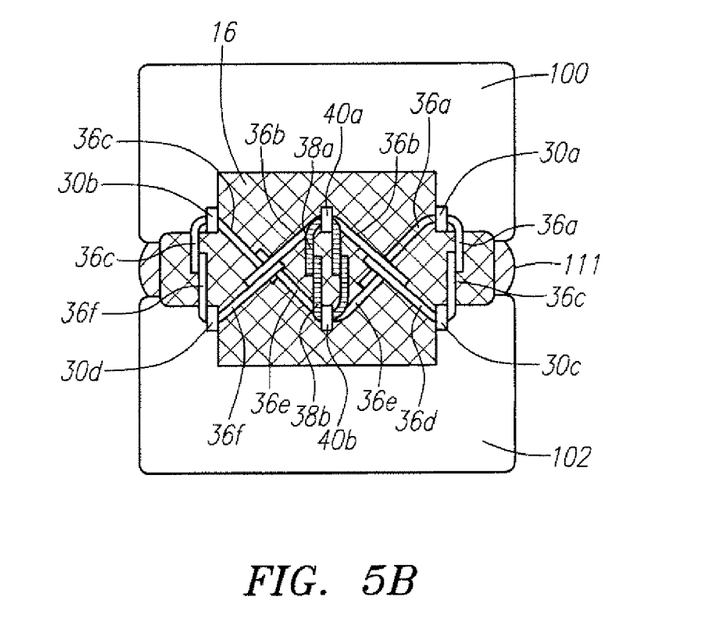
FIG. 5B is an anterior view of the embodiment in FIG. 5A showing the first sutures welded together in a cross-braced pattern and the second sutures welded together in a vertical pattern.

In some embodiments, one or more of the multiple suture anchors in each vertebra can have two sutures extending therethrough for providing additional fixation arms across the two vertebrae. In one embodiment, as shown in FIG. 5A, the central pair of anchors 40*a,b* each have two sutures 36*a,b* and 38*a,b* extending therethrough. As shown in FIG. 5B, sutures 36*a-f* are arranged as described above in FIG. 4B with lateral ends of sutures 36*a,c,d,f* creating lateral vertical fixation arms and median ends of sutures 36*a,c,d,f* and both ends of sutures 36*b,e* creating diagonal fixation arms. In addition, first and second ends of sutures 38*a,b* are welded together to create central vertical fixation arms. Tension can be applied to the sutures prior to joining them together to vary the resistance to spinal extension, lateral bending and axial rotation extension as necessary. A piece of porous mesh material 16 can be placed between the fixation sutures 36*a-f* and 38*a,b* and the spine before welding the sutures 36*a-f* and 38*a,b* together. As discussed above in detail with respect to the embodiments in FIGS. 2A-D, an anti-adhesion cover, such as ePTFE can be placed over the exposed portions of the suture anchors 30*a-d*, 40*a,b* and sutures 36*a-f* and 38*a,b* to protect the suture welds from peeling forces due to friction from adjacent structures and to help prevent injury to delicate structures such as nerves, blood vessels, and the esophagus that lie directly over the stiff ends of the sutures and exposed portions of the suture anchors.

Here, the second sutures 38*a,b* can be made of a different material than sutures 36*a-f* and thus have different properties. For example, sutures 38*a,b* can be reabsorbable, but have a higher initial breakage strength while sutures 36*a-f* are more elastic with a lower breakage strength. This pattern could be advantageous for providing an increased resistance to spinal extension during the initial period after a total disc replacement 101 has been inserted into the disc space and thereby increasing the chances for a successful replacement. Over time, the stiffer central vertical fixation arms will be reabsorbed, leaving only the more elastic diagonal and lateral fixation arms in place. These fixation arms 36*cf*, 36*ad*, and 36*ae,bd,bf,ce* could be welded under only slight tension. In addition, the fixation arms 36*cf*, 36*ad*, and 36*ae,bd,bf,ce* could be applied with the spine in an extended position. Slight tension of the fixation arms and applying the sutures with the spine in an extended position will enable full normal movement of the spine while preventing excessive extension, excessive axial rotation and excessive lateral bending of the spine.

Figure 6A:
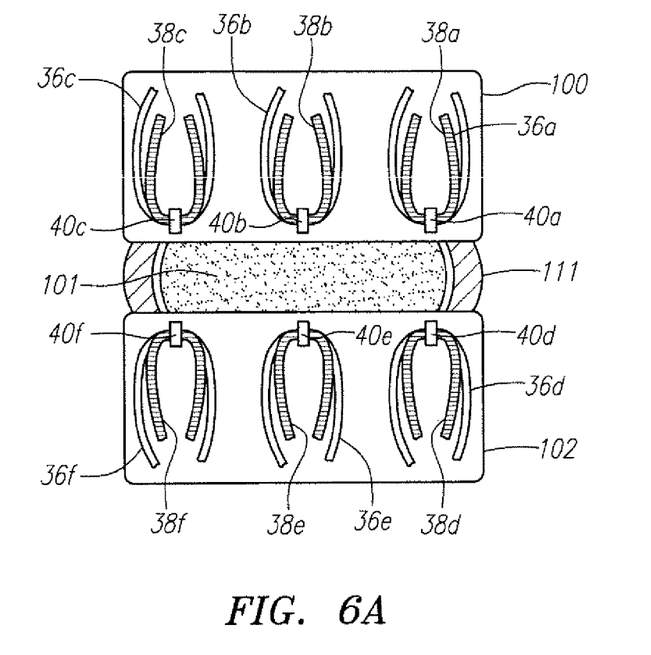
FIG. 6A is an anterior view of an alternative embodiment for joining two adjacent vertebrae using three anchors in each vertebrae and using two sutures in each suture anchor.

In an alternative embodiment, each of the multiple suture anchors in each vertebra can have two or more sutures extending therethrough for providing additional fixation arms across the two vertebrae. For example, as shown in FIG. 6A, each anchor 40*a-f* in vertebrae 100, 102 has two openings for receiving two sutures through each anchor 40*a-f*. Sutures 36*a-f* and 38*a-f* have been threaded through the two openings in each anchor 40*a-f*, Alternatively, more than two sutures could be inserted into one or more of the anchors to provide additional fixation members across a portion of the two vertebrae. As discussed above, each of the two or more sutures 36*a-f* and 38*a-f* that extend from each anchor 40*a-f* can be made of different materials and have different breakage strength and/or different elastic properties. In some embodiments, the sutures with differing properties can be color-coded such that a surgeon can easily determine which sutures to join and how much tension to apply during an operation. For example, sutures 36*a-f* could be a first color while sutures 38*a-f* could be made of a different material and have a second color to denote their different mechanical and/or physical properties.

Figure 6B:
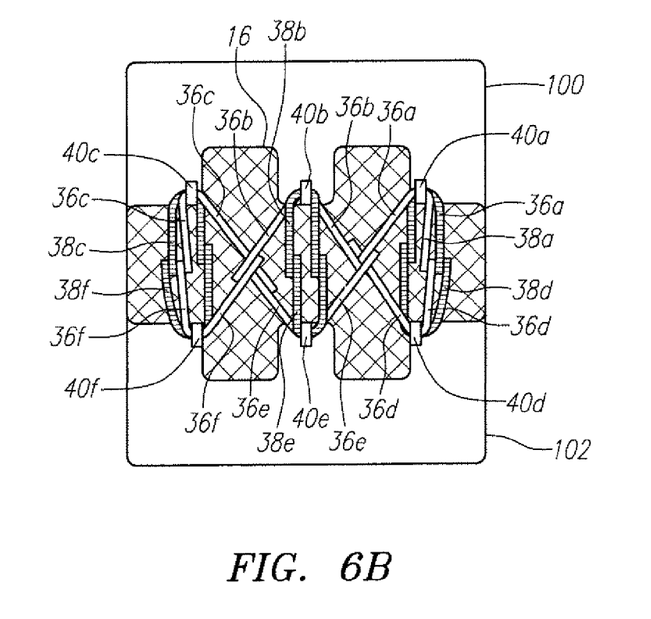
FIG. 6B is an anterior view of the embodiment in FIG. 6A showing the first sutures welded together in a cross-braced pattern and the second sutures welded together in a vertical pattern.

As shown in FIG. 6B, sutures 36*a-f* are arranged as described above in FIG. 4B with lateral ends of sutures 36*a, c,d,f* creating lateral vertical fixation arms and median ends of sutures 36*a,c,d,f* and both ends of sutures 36*b,e* creating diagonal fixation arms. In addition, first and second ends of sutures 38*a* and *d*, of 38*b* and *e* and of 38*c* and *f* are welded together to create three pairs of central vertical fixation arms 38*ad*, 38*be* and 38*cf*. Tension can be applied to the sutures prior to joining them together. The tension applied to each suture prior to welding can be varied depending on the breakage strength of the suture material and the desired resistance to motion in a certain direction. A piece of porous mesh material 16 can be placed between the fixation sutures 36*a-f* and 38*a-f* and the spine before welding the sutures 36*a-f* and 38*a-f* together. As discussed above in detail with respect to the embodiments in FIGS. 2A-D, an anti-adhesion cover, such as ePTFE can be placed over the exposed portions of the suture anchors 40*a-f* and sutures 36*a-f*, 38*a-f* to protect the suture welds from peeling forces due to friction from adjacent structures and helps prevent injury to delicate structures such as nerves, blood vessels, and the esophagus that lie directly over the stiff ends of the sutures and exposed portions of the suture anchors.

Here, the second sutures 38*a-f* can be made of a different material than sutures 36*a-f* and thus have different properties. For example, sutures 38*a-f* can be reabsorbable, but have a higher initial breakage strength while sutures 36*a-f* are more elastic with a lower breakage strength. As discussed above, this pattern could be advantageous for providing an increased resistance to spinal extension during the initial period after an intradiscal device 101 has been inserted into the disc space between vertebrae 100,102. For example as shown in FIG. 6A, where intradiscal device 101 is a nucleus replacement (NR) device the three additional vertical fixation arms 38*cf*, 38*be*, 38*ad* can advantageously provide additional resistance to spinal extension to allow the annulus fibrosis 111 to heal, thereby increasing the chances for a successful nucleus replacement.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for stabilizing a spinal segment, comprising the steps of:

providing first, second, third, fourth, fifth, and sixth anchors, wherein each anchor carries a first elongate cable terminating in distinct first and second ends that extend from each anchor;

attaching the first anchor to a first vertebra, attaching the second anchor to the first vertebra, and attaching the third anchor to the first vertebra between the first and second anchors;

attaching the fourth anchor to a second vertebra, and attaching the fifth anchor to the second vertebra, and attaching the sixth anchor to the second vertebra between the fourth and fifth anchors; and attaching each of the first and second ends of the first elongate cable of the first anchor to create an attachment with one of the first and second ends of the first elongate cable of the fourth and sixth anchors, attaching each of the first and second ends of the first elongate cable of the second anchor to create an attachment with one of the first and second ends of the first elongate cable of the fifth and sixth anchors, attaching each of the first and second ends of the first elongate cable of the fourth anchor to create an attachment with one of the first and second ends of the first elongate cable of the first and third anchors, attaching each of the first and second ends of the first elongate cable of the fifth anchor to create an attachment with one of the first and second ends of the first elongate cable of the second and third anchors, wherein at least some of the first elongate cables are attached in a crossing pattern having left and right generally vertically extending segments and diagonal connections between upper and lower end regions of each vertically extending segment.

2. The method of claim 1, wherein each step of attaching is accomplished by welding.

3. The method of claim 1, further comprising the step of removing at least a portion of the annulus fibrosis between a first vertebra and a second vertebra.

4. The method of claim 3, further comprising the step of inserting a total disc replacement device between a first vertebra and a second vertebra.

5. The method of claim 1, wherein the third and sixth anchors each carry a second elongate cable having first and second ends that extend from the third and sixth anchors.

6. The method of claim 5, further comprising the steps of attaching each of the first and second ends of the second elongate cable of the third anchor to create an attachment with one of the first and second ends of the second elongate cable of the sixth anchor.

7. The method of claim 1, further comprising the step of attaching an elongate cable to the third anchor and the sixth anchor and tightening the elongate cable to apply tension between the third anchor and the sixth anchor.

8. The method of claim 1, wherein the first and fourth anchors each carry a second elongate cable having first and second ends that extend from the first and fourth anchors.

9. The method of claim 8, further comprising the steps of attaching each of the first and second ends of the second elongate cable of the first anchor to create an attachment with one of the first and second ends of the second elongate cable of the fourth anchor.

10. The method of claim 1, further comprising the step of attaching an elongate cable to the first anchor and the fourth anchor and tightening the elongate cable to apply tension between the first and fourth anchors.

11. The method of claim 1, wherein the second and fifth anchors each carry a second elongate cable having first and second ends that extend from the second and fifth anchors.

12. The method of claim 11, further comprising the steps of attaching each of the first and second ends of the second elongate cable of the second anchor to create an attachment with one of the first and second ends of the second elongate cable of the fifth anchor.

13. The method of claim 1, further comprising the step of attaching an elongate cable to the second anchor and the fifth anchor and tightening the elongate cable to apply tension between the second and fifth anchors.

14. A method for stabilizing a spinal segment, comprising the steps of:
providing first, second, third, fourth, fifth, and sixth anchors, wherein each anchor carries a first elongate cable terminating in distinct first and second ends that extend from each anchor and wherein the third and fourth anchors each carry a second elongate cable terminating in distinct first and second ends that extend from the third and fourth anchors;

attaching the first anchor to a first vertebra, attaching the second anchor to the first vertebra, attaching the third anchor to a second vertebra, attaching the fourth anchor to the second vertebra, attaching the fifth anchor to a third vertebra, and attaching the sixth anchor to the third vertebra; and attaching each of the first and second ends of the first elongate cable of the first anchor to create an attachment with one of the first and second ends of one of the first or second elongate cables of the second, third, and fourth anchors, attaching each of the first and second ends of the first elongate cable of the second anchor to create an attachment with one of the first and second ends of one of the first or second elongate cables of the first, third, and fourth anchors, attaching each of the first and second ends of the first and second elongate cables of the third anchor to create an attachment with one of the first and second ends of the first elongate cable of the first, second, fourth, fifth, and sixth anchors, attaching each of the first and second ends of the first and second elongate cables of the fourth anchor to create an attachment with one of the first and second ends of the first elongate cable of the first, second, third, fifth, and sixth anchors.

15. The method of claim 14, wherein each step of attaching is accomplished by welding.

16. The method of claim 14, further comprising the step of placing a mesh patch between the elongate cables and the annulus fibrosis.

17. The method of claim 14, further comprising the step of placing an anti-adhesive patch covering over the elongate cables.

18. The method of claim 14, wherein the fifth and sixth anchors are attached to the third vertebra in a separate operation from the procedure wherein the first anchor and second anchors are attached to the first vertebra and the third and fourth anchors are attached to the second vertebra.

19. A method for stabilizing a spinal segment, comprising the steps of:
providing first, second, third, fourth, fifth, and sixth anchors, wherein each anchor carries a first elongate cable terminating in distinct first and second ends that extend from each anchor and a second elongate cable terminating in distinct first and second ends that extend from each anchor;

attaching the first anchor to a first vertebra, attaching the second anchor to the first vertebra, attaching the third anchor to a second vertebra, attaching the fourth anchor to the second vertebra, attaching the fifth anchor to a third vertebra, and attaching the sixth anchor to the third vertebra; and attaching each of the first and second ends of the first and second elongate cables of the first anchor to create an attachment with one of the first and second ends of one of the first or second elongate cables of the second, third, fourth, fifth, or sixth anchors, attaching each of the first and second ends of the first and second elongate cables of the second anchor to create an attachment with one of the first and second ends of one of the first or second elongate cables of the first, third, fourth, fifth, or sixth anchors, attaching each of the first and second ends of the first and second elongate cables of the third anchor to create an attachment with one of the first and second ends of the first or second elongate cables of the first, second, fourth, fifth, and sixth anchors, attaching each of the first and second ends of the first and second elongate cables of the fourth anchor to create an attachment with one of the first and second ends of the first or second elongate cable of the first, second, third, fifth, and sixth anchors.

20. The method of claim 19, wherein each step of attaching is accomplished by welding.

21. The method of claim 19, further comprising the step of placing a mesh patch between the elongate cables and the annulus fibrosis.

22. The method of claim 19, further comprising the step of placing an anti-adhesive patch covering over the elongate cables.

* * * * *